United States Patent
Gupta et al.

(10) Patent No.: US 11,832,830 B2
(45) Date of Patent: Dec. 5, 2023

(54) DEVICES, SYSTEMS, AND METHODS FOR A COATED COIL

(71) Applicant: Boston Scientific Scimed, Inc., Maple Grove, MN (US)

(72) Inventors: Ajay Gupta, Minneapolis, MN (US); Daniel K. Tomaschko, Savage, MN (US); Steven L. Kangas, Woodbury, MN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 0 days.

(21) Appl. No.: 17/530,031

(22) Filed: Nov. 18, 2021

(65) Prior Publication Data

US 2022/0151628 A1 May 19, 2022

Related U.S. Application Data

(60) Provisional application No. 63/115,898, filed on Nov. 19, 2020.

(51) Int. Cl.
*A61B 17/12* (2006.01)
*A61L 31/10* (2006.01)
(Continued)

(52) U.S. Cl.
CPC .... *A61B 17/1215* (2013.01); *A61B 17/12113* (2013.01); *A61L 31/10* (2013.01);
(Continued)

(58) Field of Classification Search
CPC .......... A61B 17/12113; A61B 17/1215; A61B 2017/00942; A61B 17/1214; A61L 31/141; A61L 31/08; A61L 31/10
See application file for complete search history.

(56) References Cited

U.S. PATENT DOCUMENTS 5,312,415 A 5/1994 Palermo
6,015,424 A * 1/2000 Rosenbluth ...... A61B 17/12113
623/1.11
(Continued)

OTHER PUBLICATIONS

Xu, Li-Chong et al. "Proteins, Platelets, and Blood Coagulation at Biomaterial Interfaces." Colloids and Surfaces B, Biointerfaces vol. 124 (2014): 49-68. doi:10.1016/j.colsurfb.2014.09.040.
(Continued)

*Primary Examiner* — Diane D Yabut
*Assistant Examiner* — Christina C Lauer
(74) *Attorney, Agent, or Firm* — Seager, Tufte & Wickhem, LLP

(57) ABSTRACT

The present disclosure relates generally to devices, systems, and methods for coil embolization, and, more particularly, to use and methods of forming coated coils. In an aspect, an embolic system may include a coil having a proximal end, a distal end, and a length therebetween slidingly disposed within a sheath. A coating may be disposed about the coil. A delivery filament may be configured to be slidingly disposed within the sheath proximal of the coil such that the coil can be ejected from the distal end of the sheath into the working lumen of a microcatheter. The coating may be configured to substantially fracture as the coil transitions from being substantially aligned with a longitudinal axis of the microcatheter to substantially misaligned with the longitudinal axis of the microcatheter upon being ejected from the microcatheter. The coating may be configured to plasticize after being ejected into an aqueous environment.

14 Claims, 9 Drawing Sheets

(51) Int. Cl.
*A61L 31/16* (2006.01)
*A61B 17/00* (2006.01)

(52) U.S. Cl.
CPC ..... *A61L 31/16* (2013.01); *A61B 2017/00526* (2013.01); *A61B 2017/00938* (2013.01); *A61B 2017/00942* (2013.01); *A61L 2300/418* (2013.01)

(56) References Cited

U.S. PATENT DOCUMENTS

| | | |
|---|---|---|
| 7,645,292 B2 | 1/2010 | Porter |
| 8,101,197 B2 | 1/2012 | Buiser et al. |
| 9,050,092 B2 | 6/2015 | Buiser et al. |
| 2007/0001346 A1 | 1/2007 | Vyakarnam et al. |
| 2009/0054965 A1* | 2/2009 | Richard ........... A61B 17/12113 623/1.49 |
| 2009/0238854 A1* | 9/2009 | Pacetti ................ A61K 47/34 424/423 |
| 2009/0297582 A1* | 12/2009 | Meyer ................ A61B 17/1215 156/60 |
| 2010/0004672 A1* | 1/2010 | Shirley ............ A61B 17/12022 427/2.24 |
| 2012/0253381 A1 | 10/2012 | Forsythe et al. |
| 2012/0330349 A1 | 12/2012 | Jones et al. |

OTHER PUBLICATIONS

International Search Report and Written Opinion dated Mar. 7, 2022 for International Application No. PCT/US2021/059918.

* cited by examiner

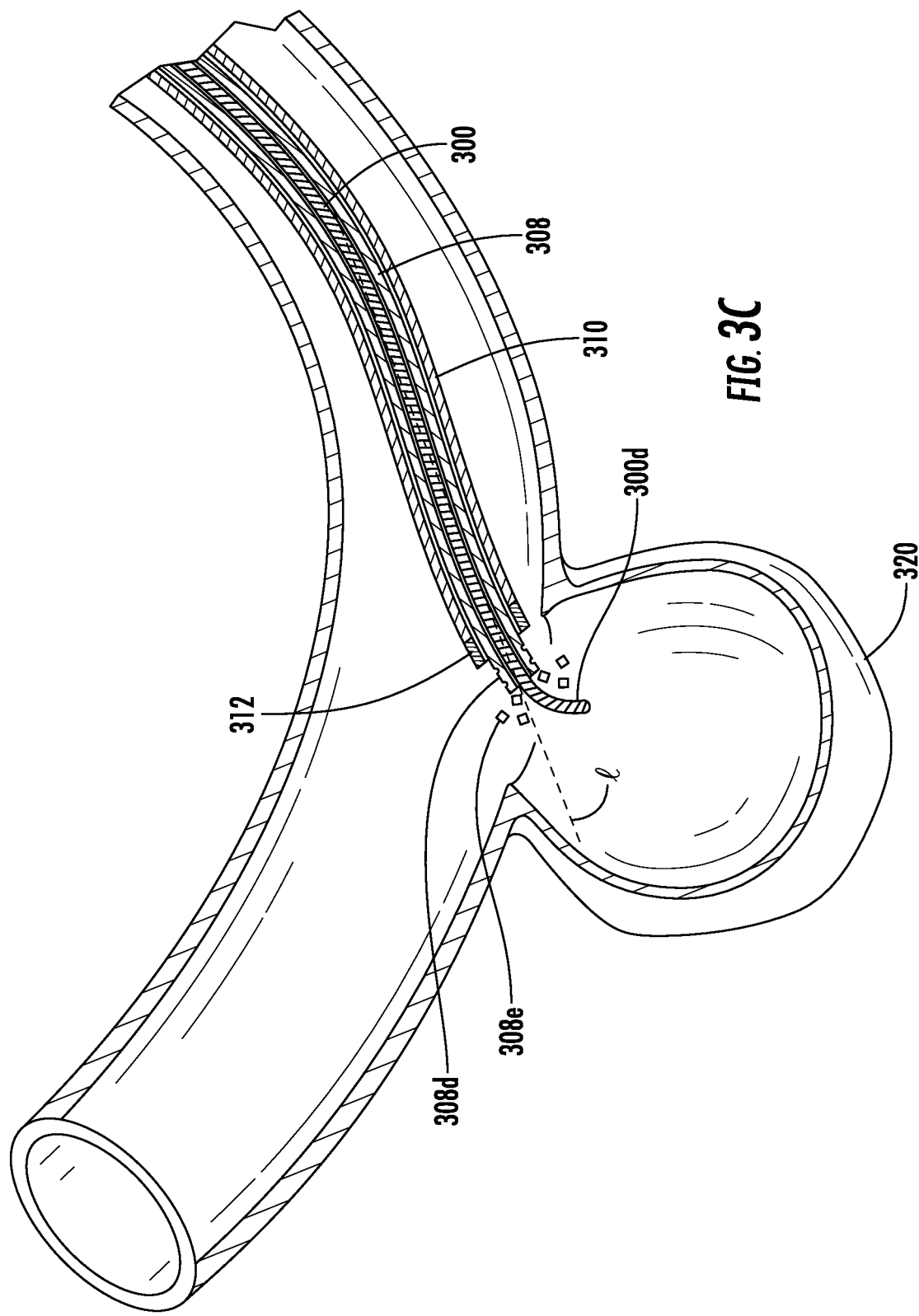

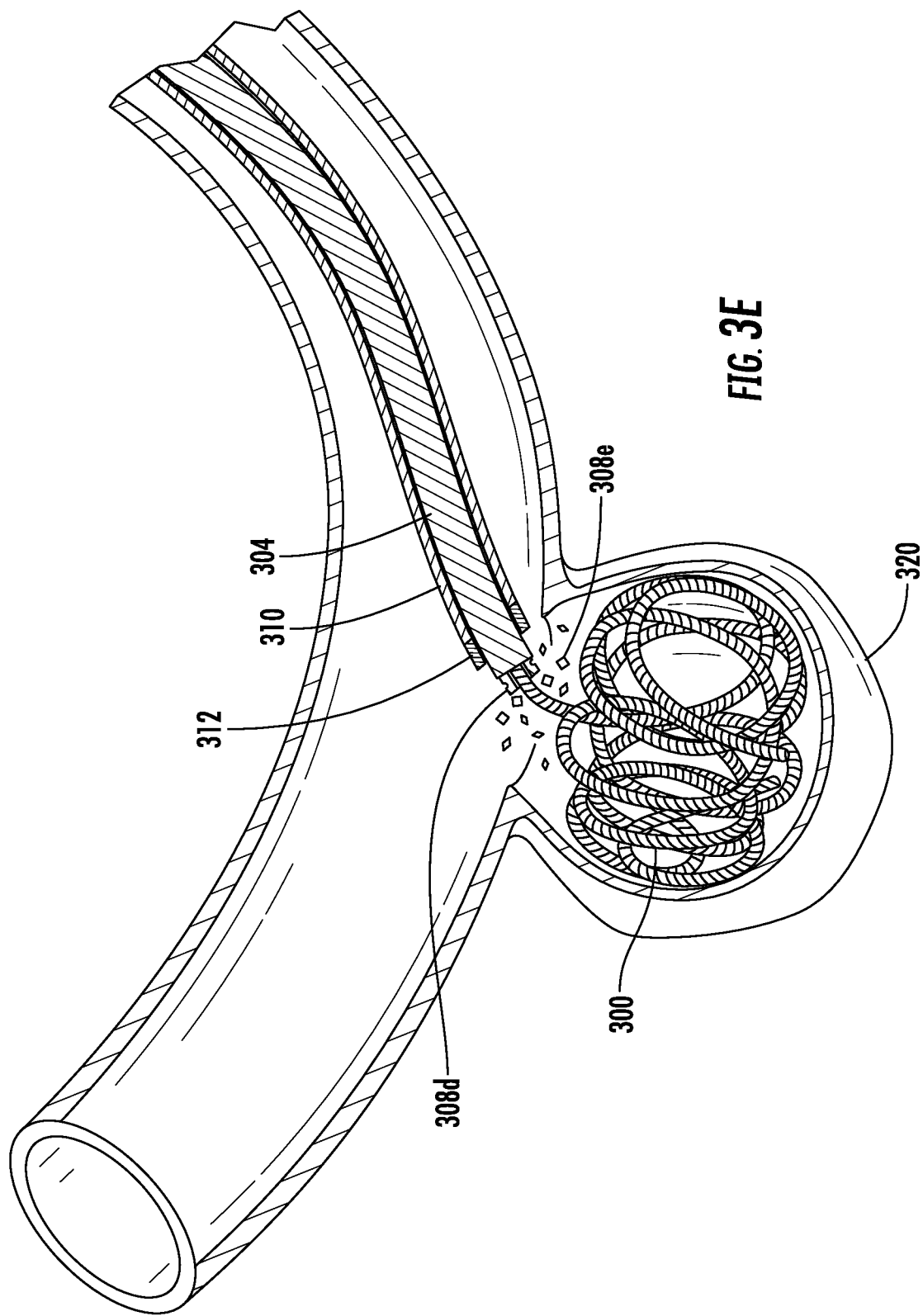

DEVICES, SYSTEMS, AND METHODS FOR A COATED COIL

PRIORITY

The present application is a non-provisional of and claims the benefit of priority under 35 USC § 119 to, U.S. Provisional Application Ser. No. 63/115,898, filed Nov. 19, 2020, the disclosure of which is hereby incorporated herein by reference in its entirety for all purposes.

FIELD

The present disclosure relates generally to devices, systems, and methods for coil embolization, and, more particularly, to use and methods of forming coated coils. Coils, such as embolic coils described herein may include material properties that may assist with rigidity, flexibility, thrombogenicity, anti-thrombogenicity, lubrication, friction, therapy, anchoring, or the like.

BACKGROUND

Therapeutic vascular occlusions (embolizations) may be used to prevent or treat pathological conditions in situ. Embolic coils may be used to occlude vessels in a variety of medical applications. Preparation, delivery, and deployment of embolic coils (e.g., into, through, and out of a catheter) may be difficult depending on the size, shape, flexibility, fragileness, etc., of the coils and/or associated delivery devices. It is with respect to these and other considerations that the present disclosure may be useful.

SUMMARY

In one aspect of the present disclosure, an embolic system may include a microcatheter comprising a proximal end, a distal end, a longitudinal axis, and a working lumen therethrough. The system may include a sheath having a proximal end, a distal end, and a delivery lumen therethrough. The distal end of the sheath may be configured to be insertable within the working lumen at the proximal end of the microcatheter. The system may include a coil having a proximal end, a distal end, and a length therebetween slidingly disposed within the sheath. A coating may be disposed about the coil. A delivery filament may be configured to be slidingly disposed within the sheath proximal of the coil such that the coil can be ejected from the distal end of the sheath into the working lumen of the microcatheter. The delivery filament may be configured to be slidingly disposed within the working lumen of the microcatheter proximal of the coil such that the coil can be ejected from the working lumen at the distal end of the microcatheter to a target site. The coating may be configured to substantially fracture as the coil transitions from being substantially aligned with the longitudinal axis of the microcatheter to substantially misaligned with the longitudinal axis of the microcatheter upon being ejected from the microcatheter or wherein the coating may be configured to plasticize after being ejected from the distal end of the sheath into an aqueous environment.

In various embodiments described herein or otherwise within the scope of the present disclosure, the coil may include a primary shape that is substantially linear when disposed within the microcatheter and a secondary shape that is substantially curvilinear when ejected from the microcatheter to the target site. The coating may be configured to substantially fracture away from the coil as the coil transitions from the primary shape to the secondary shape. The coating may be formed from a hydrophilic polymer having a number average molecular weight of about 10,000 g/mol to about 1,000,000 g/mol. The coating may be disposed about an outer surface of the coil. The coil may include a polymer and the coating may include at least one of polyvinylpyrrolidone, polyethylene glycol, polyethylene oxide, polyvinyl alcohol, polyacrylic acid, polyacrylamide, hydroxypropyl methacrylamide, and a polyamine. The coating may include a hydrophilic polymer and wherein the coating is configured to substantially fracture upon being ejected from the microcatheter. The coil may include a polymer and the coating may include at least one of xanthan gum, pectin, chitosan, sodium alginate, sodium carboxymethylcellulose, hydroxypropylcellulose, hyaluronic acid, dextran, carrageenan, guar gum, cellulose ether, albumin, a starch, polylactic acid homopolymer, polyglycolic acid homopolymer, a copolymer of lactic acid, a copolymer of glycolic acid (PLGA), polycaprolactone, polyhydroxybutyric acid, polyhydroxyalkanoate, and aliphatic polyester. The coating may include a hydrophobic polymer and wherein the coating is configured to plasticize after being ejected from the distal end of the sheath into an aqueous environment. The coil may include a pro-thrombogenic factor covered by the coating. The delivery filament may include a distal end reversibly coupled to the proximal end of the coil. At least one fiber may be coupled to the coil and disposed within the coating.

In one aspect of the present disclosure, an embolic coil may include a coil filament arranged in adjacent windings about a longitudinal axis. A coating may be disposed about the windings. The coating may be a frangible coating may be configured to fracture away from the windings of a portion of the coil as the portion of the coil transitions from being substantially aligned with the longitudinal axis of a remainder of the coil, or wherein the coating may be configured to plasticize after being ejected into an aqueous environment.

In various embodiments described herein or otherwise within the scope of the present disclosure, the coating may include at least one of polyvinylpyrrolidone, polyethylene glycol, polyethylene oxide, polyvinyl alcohol, polyacrylic acid, polyacrylamide, hydroxypropyl methacrylamide, and a polyamine. The coating may include a hydrophilic polymer and wherein the coating is a frangible coating configured to fracture as the portion of the coil transitions from being substantially aligned with the longitudinal axis of the remainder of the coil. The frangible coating may include at least one of xanthan gum, pectin, chitosan, sodium alginate, sodium carboxymethylcellulose, hydroxypropylcellulose, hyaluronic acid, dextran, carrageenan, guar gum, cellulose ether, albumin, a starch, polylactic acid homopolymer, polyglycolic acid homopolymer, a copolymer of lactic acid, a copolymer of glycolic acid (PLGA), polycaprolactone, polyhydroxybutyric acid, polyhydroxyalkanoate, and aliphatic polyester. The coating may include a hydrophobic polymer and wherein the coating is configured to plasticize after being ejected into an aqueous environment. The coil filament may include a primary shape that is substantially linear and a secondary shape that is substantially curvilinear. The coating may be configured to substantially fracture away from the coil filament as the coil filament transitions from the primary shape to the secondary shape. The coating may be substantially insoluble while disposed about the windings. The coating may be substantially soluble while fractured away from the windings. The coating may be a lower coefficient of friction than the coil filament. A sheath may include a proximal end, a distal end, and a delivery lumen therethrough. The coil may be slidingly disposed within the sheath. The frangible coating may include a hydrophilic polymer having a number average molecular weight of about 10,000 g/mol to about 1,000,000 g/mol.

In one aspect of the present disclosure, a method of forming a coil may include winding a coil filament into adjacent windings about a longitudinal axis. The coil filament may be submerged into a container holding a fluid comprising a hydrophilic polymer having a number average molecular weight of about 10,000 g/mol to about 1,000,000 g/mol. An end of the coil filament may be lifted out of the container until an opposing end of the coil filament ascends out of the fluid.

In various embodiments described herein or otherwise within the scope of the present disclosure, lifting the end of the coil filament may further include holding the end of the coil filament such that it is substantially aligned with each of the longitudinal axis and the opposing end of the coil filament. The adjacent windings of the coil filament may be heat set into a secondary shape. The fluid may include at least one of polyvinylpyrrolidone, polyethylene glycol, polyethylene oxide, polyvinyl alcohol, polyacrylic acid, polyacrylamide, hydroxypropyl methacrylamide, and a polyamine. The fluid may include a hydrophilic polymer and wherein the coating is configured to substantially fracture upon being ejected from the microcatheter. The fluid may include at least one of xanthan gum, pectin, chitosan, sodium alginate, sodium carboxymethylcellulose, hydroxypropyl-cellulose, hyaluronic acid, dextran, carrageenan, guar gum, cellulose ether, albumin, and a starch. The fluid may include a hydrophobic polymer and wherein the coating is configured to plasticize after being ejected from the distal end of the sheath into an aqueous environment.

BRIEF DESCRIPTION OF THE DRAWINGS

Non-limiting embodiments of the present disclosure are described by way of example with reference to the accompanying figures, which are schematic and not intended to be drawn to scale. In the figures, each identical or nearly identical component illustrated is typically represented by a single numeral. For purposes of clarity, not every component is labeled in every figure, nor is every component of each embodiment shown where illustration is not necessary to allow those of ordinary skill in the art to understand the disclosure. In the figures:

FIG. 3C schematically illustrates the coil of the embolic system of FIG. 3A being delivered at a first point in time, according to an embodiment of the present disclosure.

FIG. 3E schematically illustrates the coil of the embolic system of FIG. 3A being deployed at a third point in time, according to an embodiment of the present disclosure.

DETAILED DESCRIPTION

Figure 1:
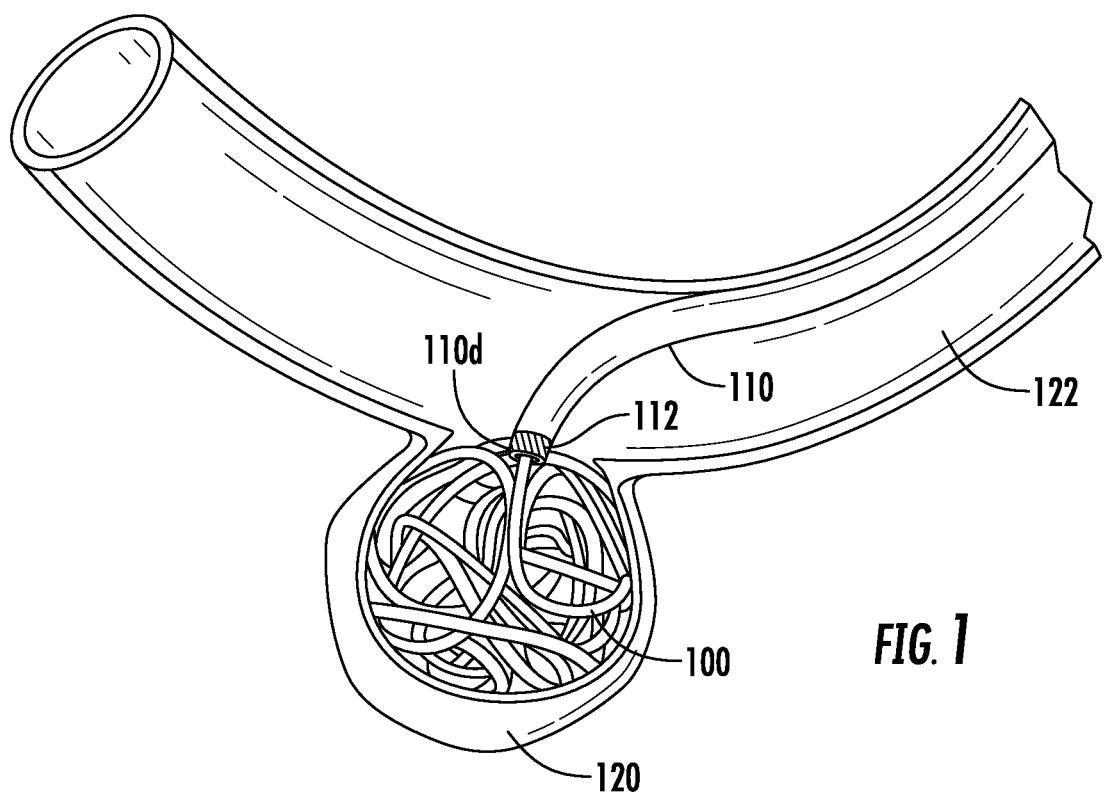
FIG. 1 schematically illustrates an embolic coil being deployed, according to an embodiment of the present disclosure.

The present disclosure is not limited to the particular embodiments described. The terminology used herein is for the purpose of describing particular embodiments only and is not intended to be limiting beyond the scope of the appended claims. Unless otherwise defined, all technical terms used herein have the same meaning as commonly understood by one of ordinary skill in the art to which the disclosure belongs.

Although embodiments of the present disclosure may be described with specific reference to medical devices and systems (e.g., embolic devices and/or accessory tools within vasculature or the like), it should be appreciated that such medical devices and systems may be used in a variety of medical procedures for occlusion, anchoring, scaffolding, and the like. The medical devices herein may include a variety of medical devices for navigating patient anatomy, including, e.g., catheters, microcatheters, visualization devices (e.g., fluoroscopic, ultrasonic, x-ray, endoscope, etc.) that may be inserted via different access points and approaches, e.g., percutaneously, endoscopically, laparoscopically, or combinations thereof.

As used herein, the term "coil" is intended to include occlusion devices such as for embolization. Such occlusion devices may be intended for aneurysms, blood vessels, tumors, other vasculature, or other body lumens.

As used herein, the singular forms "a," "an," and "the" are intended to include the plural forms as well, unless the context clearly indicates otherwise. The terms "comprises" and/or "comprising," or "includes" and/or "including" when used herein, specify the presence of stated features, regions, steps, elements and/or components, but do not preclude the presence or addition of one or more other features, regions, integers, steps, operations, elements, components and/or groups thereof.

As used herein, "proximal end" refers to the end of a device that lies closest to the medical professional along the device when introducing the device into a patient, and "distal end" refers to the end of a device or object that lies furthest from the medical professional along the device during implantation, positioning, or delivery.

As used herein, the conjunction "and" includes each of the structures, components, features, or the like, which are so conjoined, unless the context clearly indicates otherwise, and the conjunction "or" includes one or the others of the structures, components, features, or the like, which are so conjoined, singly and in any combination and number, unless the context clearly indicates otherwise.

All numeric values are herein assumed to be modified by the term "about," whether or not explicitly indicated. The term "about", in the context of numeric values, generally refers to a range of numbers that one of skill in the art would consider equivalent to the recited value (i.e., having the same function or result). In many instances, the term "about" may include numbers that are rounded to the nearest significant figure. Other uses of the term "about" (i.e., in a context other than numeric values) may be assumed to have their ordinary and customary definition(s), as understood from and consistent with the context of the specification, unless otherwise specified. The recitation of numerical ranges by endpoints includes all numbers within that range, including the endpoints (e.g., 1 to 5 includes 1, 1.5, 2, 2.75, 3, 3.80, 4, and 5).

It is noted that references in the specification to "an embodiment", "some embodiments", "other embodiments", etc., indicate that the embodiment(s) described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it would be within the knowledge of one skilled in the art to affect such feature, structure, or characteristic in connection with other embodiments, whether or not explicitly described, unless clearly stated to the contrary. That is, the various individual elements described below, even if not explicitly shown in a particular combination, are nevertheless contemplated as being combinable or arrangeable with each other to form other additional embodiments or to complement and/or enrich the described embodiment(s), as would be understood by one of ordinary skill in the art.

With reference to FIG. 1, a coil 100 is illustrated being deployed into an aneurysm 120 according to an embodiment of an embolic system of the present disclosure. The system shown includes a microcatheter 110 extended within a blood vessel 122 with a distal end 110d of the microcatheter 110 being oriented toward the aneurysm 120 for treatment. The distal end 110d of the microcatheter 110 may be manipulated under observation by, e.g., visualizing a radiopaque band 112 via fluoroscopy, among other possible techniques. The coil 100 is being distally deployed from the microcatheter 110 to generally fill a volume of the aneurysm 120.

In various embodiments described herein, a coil may be desirably flexible for deployment and filling of an aneurysm. However, such a flexible coil may have complications during delivery through a microcatheter, e.g., the coil may prolapse, buckle, or be crushed by proximal member axially pushing the coil distally through the microcatheter. These complications may be addressed providing a coating described herein on a coil having a greater axial stiffness than the underlying coil, which may assist with the pushability of the coil through the microcatheter, reducing these complications. However, such stiffness may be undesirable during deployment of the coil, e.g., into an aneurysm. Therefore, it may be desirable for the coil to substantially lose the coating upon deployment after the coil has been delivered through the microcatheter.

In various embodiments described herein, a coil may include a coating disposed about an external surface of the coil, about all surfaces of the coil, and/or within and throughout the coil. The coating may include materials that temporarily alter properties of the coil, e.g., for preparation, delivery, and/or deployment, that may include therapeutic properties such as drug delivery or that may assist with, inhibit, or accelerate bodily functions, e.g., thrombosis. A coating may reduce friction of the coil during delivery, e.g., by including lubrication or reducing surface area such as encapsulating and/or repositioning fibers extending from the coil. Such coatings may remain on the coil for extended periods or may instead be bioerodable, frangible, or soluble such that the coating is removed from the coil during preparation, delivery, and/or deployment, or shortly thereafter (e.g., before removal of a microcatheter delivering or deploying the coil).

Figure 2A:
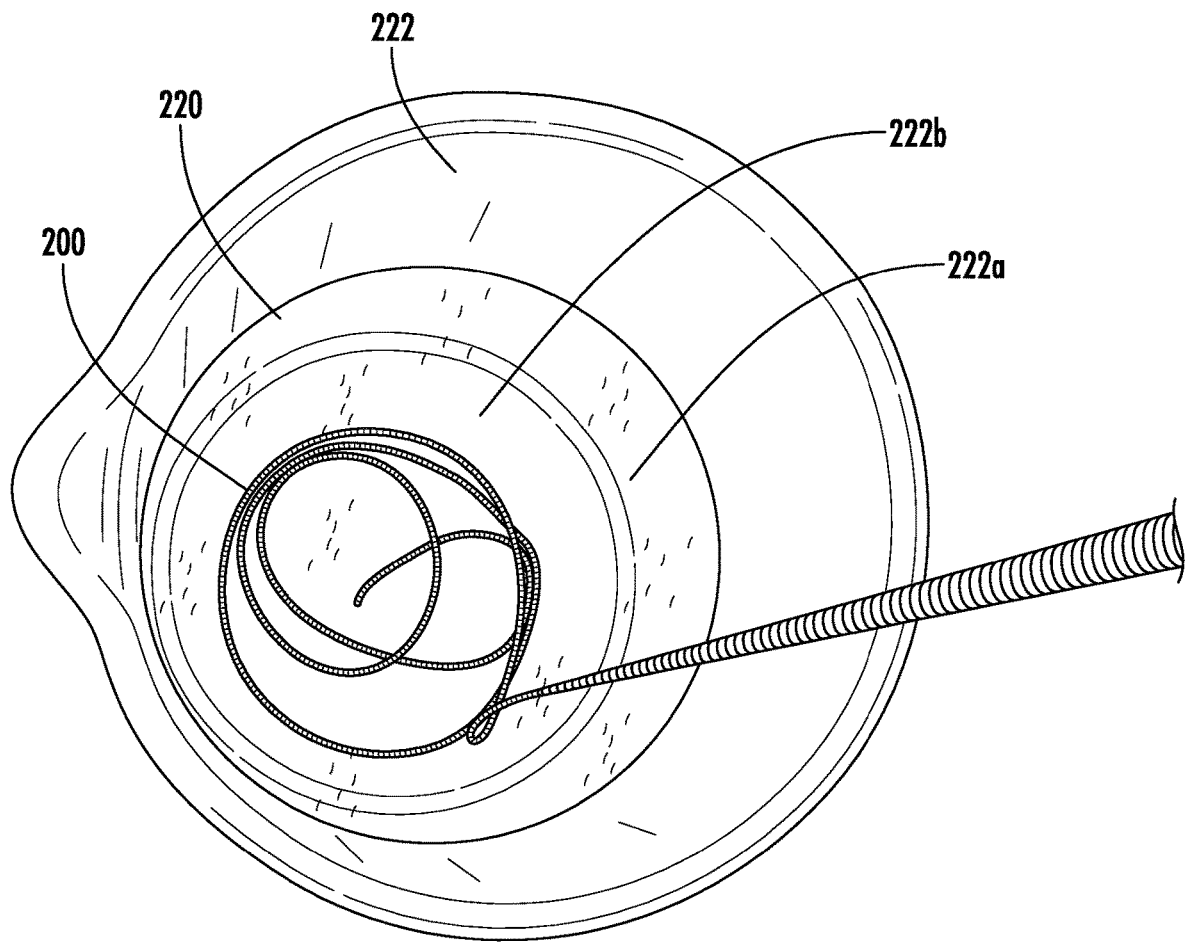
FIG. 2A schematically illustrates an embolic coil being submerged into a fluid, according to an embodiment of the present disclosure.

Referring to FIG. 2A a coating is being formed on a coil 200 according to an embodiment of a method of the present disclosure. The coil 200 is being submerged into a fluid 220 contained within a reservoir 222. The fluid 220 comprises material(s) described herein intended to coat the coil 200. The coil 200 may be submerged into the fluid 220 at a uniform pace such that the fluid 220 contacts or adheres to substantially all of the external surfaces of the coil 200 before the coil 200 contacts a bottom 222b of the reservoir 222 and/or before the coil 200 contacts itself. The coil 200 may be submerged into the reservoir 222 such that portions of the coil 200 make minimal contact with the side 222s of the reservoir 222, which may assist with maximizing contact between the fluid 220 and surfaces of the coil 200. The entire length of the coil 200 may be submerged in the fluid 220 such that substantially all surfaces or all exposed or external surfaces of the coil 200 are in contact with the fluid 220. The length of the coil 200 may be submerged for a period of time such that the fluid 220 covers, adheres, and/or bonds to the coil 200.

Figure 2B:
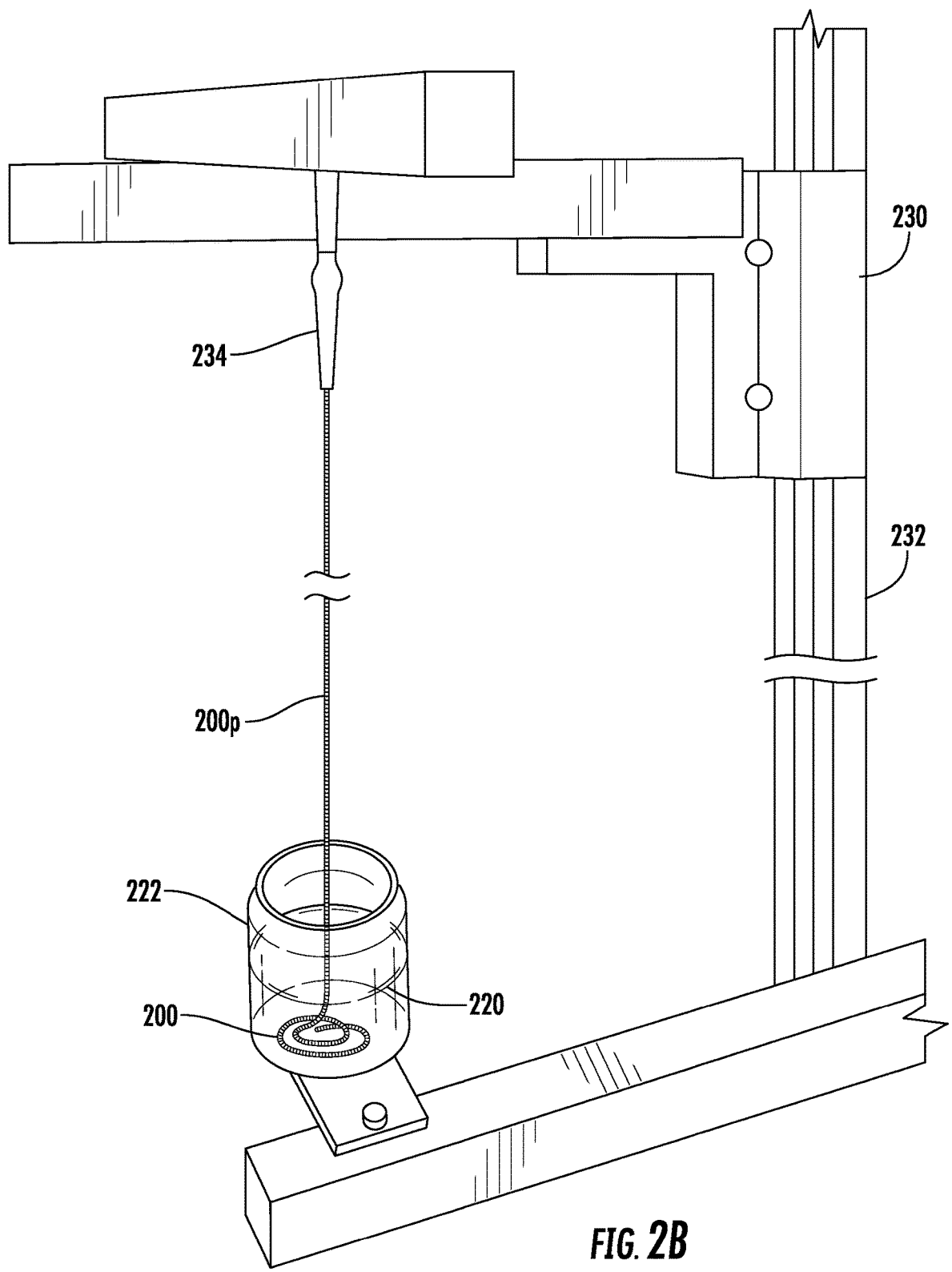
FIG. 2B schematically illustrates the embolic coil of FIG. 2A being removed from the fluid.

Referring to FIG. 2B the coating being formed on the coil 200 of FIG. 2A is illustrated with the coated coil 200 being removed from the reservoir 222. The coil 200 is completely submerged within the fluid 220 (i.e., via the process of FIG. 2A) such that the surfaces of the coil 200 are adequately contacted with the fluid 220. The coil 200 may be removed from the fluid 220 by grasping an end of the coil 200 with a clamp 234 and lifting the coil 200 out of the fluid 220 of the reservoir 222. The clamp 234 is coupled to an arm 230 of a gantry system that may vertically translate the arm 234 along a track 232. The clamp 234 may be positioned vertically over the reservoir 222 such that as the coil 200 ascends from the reservoir 222, such that further contact between the coil 200 and the reservoir 222 is substantially avoided. As the coil 200 ascends from the fluid 220, a portion 200p of the coil 200 is exposed to the atmosphere and is longitudinally aligned along its length over the reservoir 222. This longitudinal alignment forms a substantially straight coated coil 200 and may allow some fluid 220 to flow along the length of the coil 200 for coating and/or flowing into the reservoir 222 via gravity as the fluid 220 dries and/or bonds. The coil 200 may be removed from the fluid 220 and the reservoir 222 at a uniform pace (e.g., vertically ascending along a length of the coil 200 at a rate of about 1 mm/s to about 25 mm/s, which may vary by desired coating thickness, solids percentage of the fluid or coating, viscosity, or the like). The coil 200 may be entirely removed from the fluid 220 and held by the clamp 234 over the reservoir 222 such that the coating forms along the length of the coil 200 with the coil 200 substantially straightened along its longitudinal axis (e.g., with an end of the coil 200 positioned vertically above an opposing end of the coil 200 once fully ascended). The coil 200 may be held by the clamp 234 over the reservoir 222 for a period of time such that the coating fully forms (e.g., completely dries, cures, etc. for a period of time, e.g., ranging at about 30 minutes to about 4 hours, e.g., at room temperature, which may be decreased by, e.g., increasing temperature using, e.g., in-line IR lamps at, e.g., about 60° C. to about 100° C., or transferring the coil 200 to a convection oven at, e.g., about 40° C. to about 100° C. for, e.g., about fifteen minutes to about one hour). Although a submerging coating (i.e., dip coating) process is illustrated, in various embodiments described herein a coil may be coated via alternative methods such as solvent coating, spray coating, coating using a brush or other applicator, or the like.

In various embodiments described herein, a coil may be formed from a filament into windings, e.g., over a mandrel, along a length of the coil and a longitudinal axis therethrough. These filament windings may form, e.g., a primary shape of the coil with the windings formed substantially linearly along the longitudinal axis. Adjacent windings may be in contact with each other or they may include gaps therebetween. Adjacent windings may be adhered together other, e.g., via melted flowing, tacking, an adhesive, a coating, or the like. The primary shape may be formed into a secondary shape, e.g., a helix, a ball, a cone, curvilinear shapes, layered shapes spaced or overlapping each other, a serpentine, a combination thereof, or the like. The secondary shape may be formed, e.g., over a mandrel and heat set such that the secondary shape creates deformations in the coil to form the secondary shape, e.g., when the coil is in freeform rather than in tension or constrained, e.g., within a sheath, a microcatheter, a coating, or the like. A coating described herein may be formed on a filament of a coil before shaping the filament, after forming the primary shape of the coil, or after forming the secondary shape of the coil. A coating may be continuous across windings of a coil.

In various embodiments described herein, a filament of a coil may comprise one or more materials, e.g., a polymer including synthetic polymers, natural polymers, cross-linked polymers, non-cross-linked polymers, thermosetting polymers, and/or thermoplastic polymers. Examples of polymers include polyolefins; polyurethanes; block copolymers (e.g., block copolymers with segments including esters, ethers and/or carbonates); polyethers; polyimides; acrylates (e.g., cyanoacrylates); epoxy adhesive materials (e.g., one-part epoxy-amine materials, two-part epoxy-amine materials); polymers and/or copolymers of ethylene, propylene, butadiene, styrene, and/or thermoplastic olefin elastomers; polydimethyl siloxane-based polymers; Rayon; cellulose; cellulose derivatives (e.g., nitrocellulose); natural rubbers; polyesters (e.g., polyethylene terephthalate); polylactides; polyglycolides; polycaprolactones; copolymers of lactides, glycolides, and/or caprolactones; polyhydroxybutyrate, polyhydroxyvalerate, and copolymers of hydroxybutyrate and hydroxyvalerate; polyether esters (e.g., polydioxanone); polyanhydrides, such as polymers and copolymers of sebacic acid, hexadecanedioic acid and other diacids; orthoesters; polyamino acids; polynucleic acids; polysaccharides; and polyhydroxyalkanoate. In various embodiments, a filament can include one or more mixtures and/or copolymers (e.g., block copolymers, random copolymers) of these materials. In various embodiments a coil may include one or more fibers extending from the coil to promote clotting or occlusion comprising one or more filament materials described herein.

In various embodiments described herein, a coating or a fluid forming a coating may comprise one or more materials, for example, one or more polymeric materials such as those listed below. In some embodiments, a solid and/or brittle coating may be insoluble and may stiffen a coil for delivery and the coating may be frangible such that the coating may fracture away from the coil into particles upon deployment, and the particles may be soluble and biocompatible when absorbed or passed through the body. A coating may be formed from a substantially water insoluble, hydrophobic polymer, e.g., having a number average molecular weight of about 1,000 g/mol to about 100,000 g/mol. The hydrophobic polymer may be biodegradable in the presence of blood where the polymer substantially degrades, e.g., in a range of about 1 week to about 1 month. The coil may include a polymer and the coating may include at least one of polylactic acid homopolymer, polyglycolic acid homopolymer and copolymers of lactic acid and glycolic acid (PLGA), polycaprolactone, polyhydroxybutyric acid, polyhydroxyalkanoate, and aliphatic polyesters, A coating may have a composition such that the coating fractures when the coil moves, bends, or deforms substantially outside of its longitudinal axis (e.g., at least a portion of a coil moving out of its longitudinally aligned or primary shape) and/or substantially outside of a longitudinal axis of a microcatheter or sheath. For example, a coating may comprise one or more hydrophilic polymers. For example, a coating may comprise one or more of a polyvinylpyrrolidone polymer or copolymer, polyethylene glycol, polyethylene oxide, polyvinyl alcohol, polyacrylic acid, copolymers of polyacrylamide, copolymers of hydroxypropyl methacrylamide, polyamines, xanthan gum, pectin, chitosan derivatives, sodium alginate, sodium carboxymethylcellulose, hydroxypropylcellulose, hyaluronic acid, dextran, carrageenan, guar gum, cellulose ethers, albumin, starch, starch-based derivatives, or the like. In some embodiments, the composition may comprise a hydrophilic polymer having a number average molecular weight ranging from about 10,000 g/mol to about 1,000,000 g/mol) In certain beneficial embodiments a coating may be formed from a polyvinylpyrrolidone (PVP) polymer having a number average molecular weight ranging from about 10,000 g/mol to about 1,000,000 g/mol.

Figure 3A:
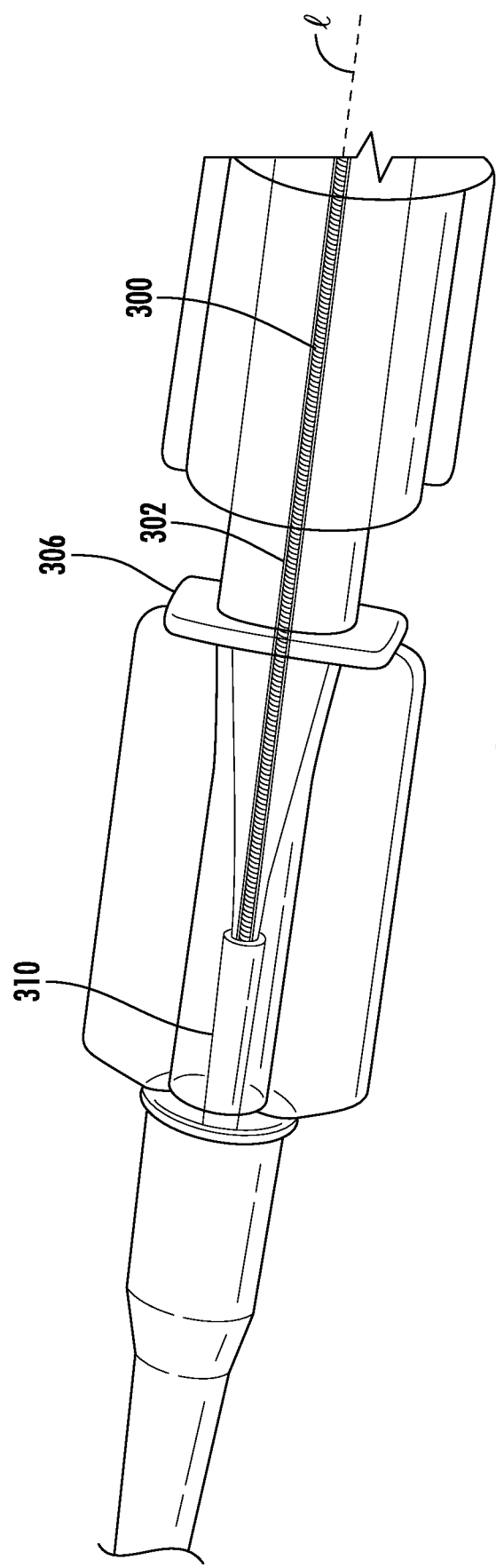
FIG. 3A schematically illustrates preparation of an embolic system including a sheath containing an embolic coil being introduced into a microcatheter, according to an embodiment of the present disclosure.

With reference to FIG. 3A, the preparation of an embodiment of an embolic system is illustrated including a sheath 302 containing a coated embolic coil 300 being introduced into a working lumen of a microcatheter 310. The sheath 302 may protect the coil 300 during packaging, e.g., from trauma or abrasions, and may assist with preparing the coil 300 for patient delivery. The coated coil 300 is in a primary shape substantially aligned along its length with a longitudinal axis $\ell$ extending through the microcatheter 310. A distal end of the sheath 302 containing the coil 300 is extending through an access hub 306 at a proximal end of the microcatheter 310. The outer diameter of the sheath 302 may substantially match an inner diameter of the microcatheter 310 such that the distal end of the sheath 302 is firmly seated within the proximal end of the microcatheter 310. Alternatively, the outer diameters of both the sheath 302 and the microcatheter 310 may substantially match such that they abut each other. In the configuration illustrated in FIG. 3A, the coil 300 is freely slidable from within the delivery lumen of the sheath 302 into the microcatheter 310, e.g., substantially along the longitudinal axis $\ell$.

Figure 3B:
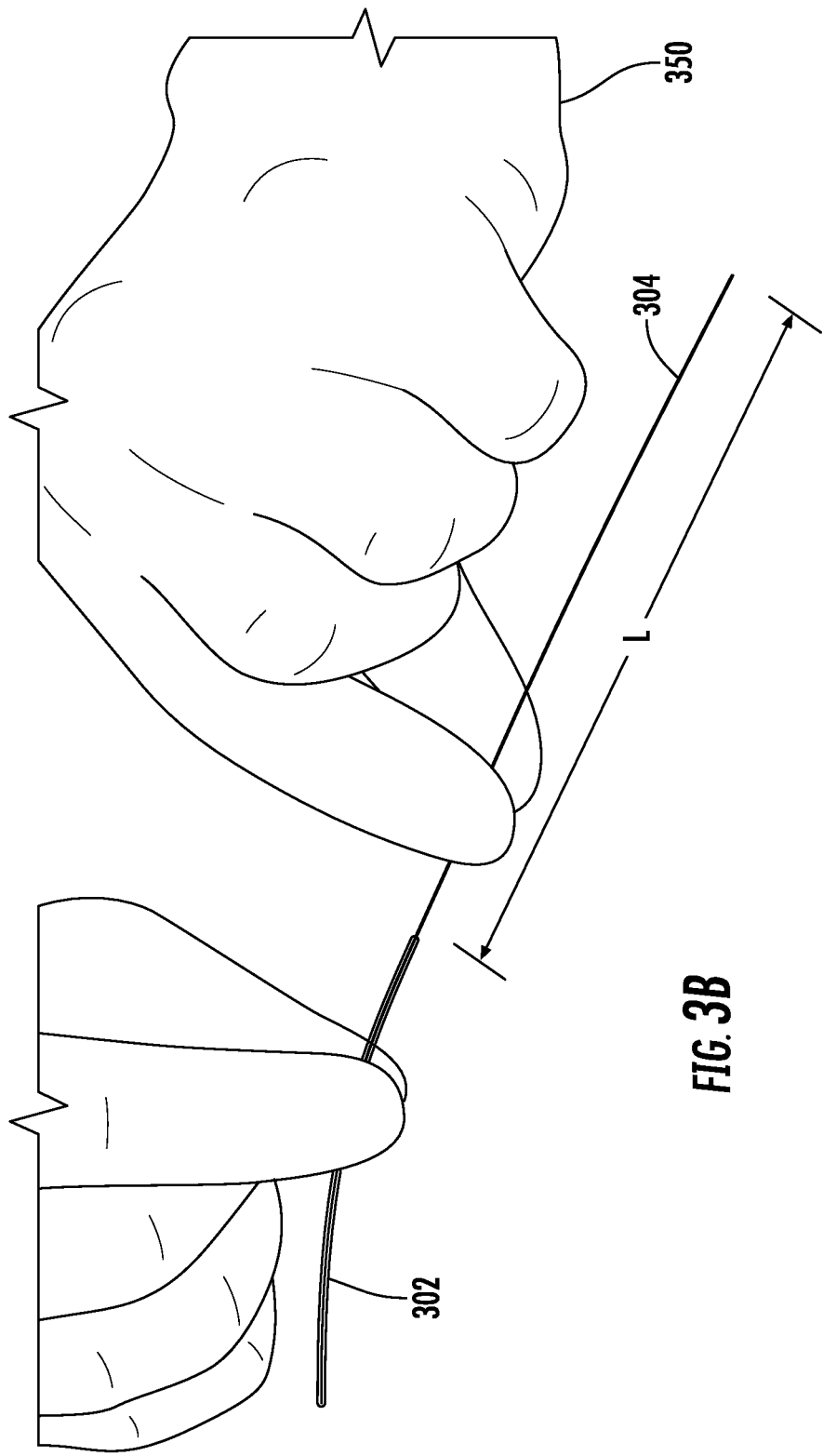
FIG. 3B schematically illustrates a delivery filament within the sheath of the embolic system of FIG. 3A, according to an embodiment of the present disclosure.

With reference to FIG. 3B, the sheath 302 of the embolic system of FIG. 3A is illustrated with a delivery filament 304 slidingly extended into the proximal end of the sheath 302. The coil 300 may be delivered from within the sheath 302 into the microcatheter 310 of FIG. 3A via distal translation of the delivery filament 304 by a medical professional 350. Further translation of the delivery filament 304 into the sheath 302 will with result in further delivery of the coil 300 into the microcatheter 310. An insertable length of the delivery filament 304 substantially matches a length of the delivery sheath 302 such that a distance L between the proximal end of the delivery filament 304 and the proximal end of the sheath 302 is substantially equivalent to a length of the coil 300 that remains within the sheath 302 (i.e., with a remainder of the length of the coil 300 being within the microcatheter 310). As the proximal end of delivery filament 304 approaches the proximal end of the sheath 302 (e.g., when L is about 10 cm or the like) the user 350 may stop translating the delivery filament 304 into the sheath 302 and may proximally withdraw the sheath 302 along the delivery filament 304 until the sheath 302 is removed from the system. The user 350 may thereafter further translate the delivery filament 304 through the hub 306 and into the microcatheter 310 to further deliver, eject, and/or deploy the coil 300 without losing the delivery filament 304 within the sheath 302 if the sheath 302 were not proximally removed.

FIG. 3C illustrates the coil 300 of the embolic system of FIGS. 3A and 3B being delivered and deployed into an aneurysm 320. The coil 300 includes a coating 308. The coated coil 300 is being distally translated through the microcatheter 310 via distal translation of the delivery filament 304 of FIG. 3B through the microcatheter 310 substantially along a longitudinal axis ℓ of the microcatheter 310 and/or a proximal portion of the coil 300. As a distal end 300d of the coil 300 distally extends out of the microcatheter 310 past a distal marking band 312 that may be visualized, e.g., a radiopaque distal marking band 312 that may be visualized via fluoroscopy, the distal end 300d is free to move partially out of general alignment (i.e., generally misaligned) with the longitudinal axis ℓ of the microcatheter 310 and/or the proximal portion of the coil 300. In various embodiments described herein, a portion of a coil may be moved out of general alignment with the longitudinal axis by, e.g., bodily fluid flow, gravity, bodily fluid contact, tissue contact, medical device contact, random chance, or a combination thereof. As the distal end 300d of the coil 300 and the coating 308 move out of the microcatheter 310 and out of general alignment with the longitudinal axis ℓ, a portion 308d of the brittle coating 308 fractures and breaks away into particles 308e away from the coil 300, although, as discussed herein including with reference to FIGS. 4-6, similar or alternative coating transitioning may occur. As the coating 308 breaks away from the coil 300, properties of the coil 300 may change as described herein. For example, the coating 308 while on the coil 300 may increase rigidity of the coil 300 so that the coil 300 is more easily pushed by the delivery filament 304 through the microcatheter 310 and, as the coating 308 breaks away from the distal end 300d of the coil 300, the coil 300 may become more flexible for deploying into the aneurism 320. Additionally, as the coating 308 fractures into particles 308e away from the coil 300, materials of both the coating 308 and the coil 300 may be exposed to the body, e.g., thrombogenic accelerants, thrombogenic fibers, or the like as described herein.

Figure 3D:
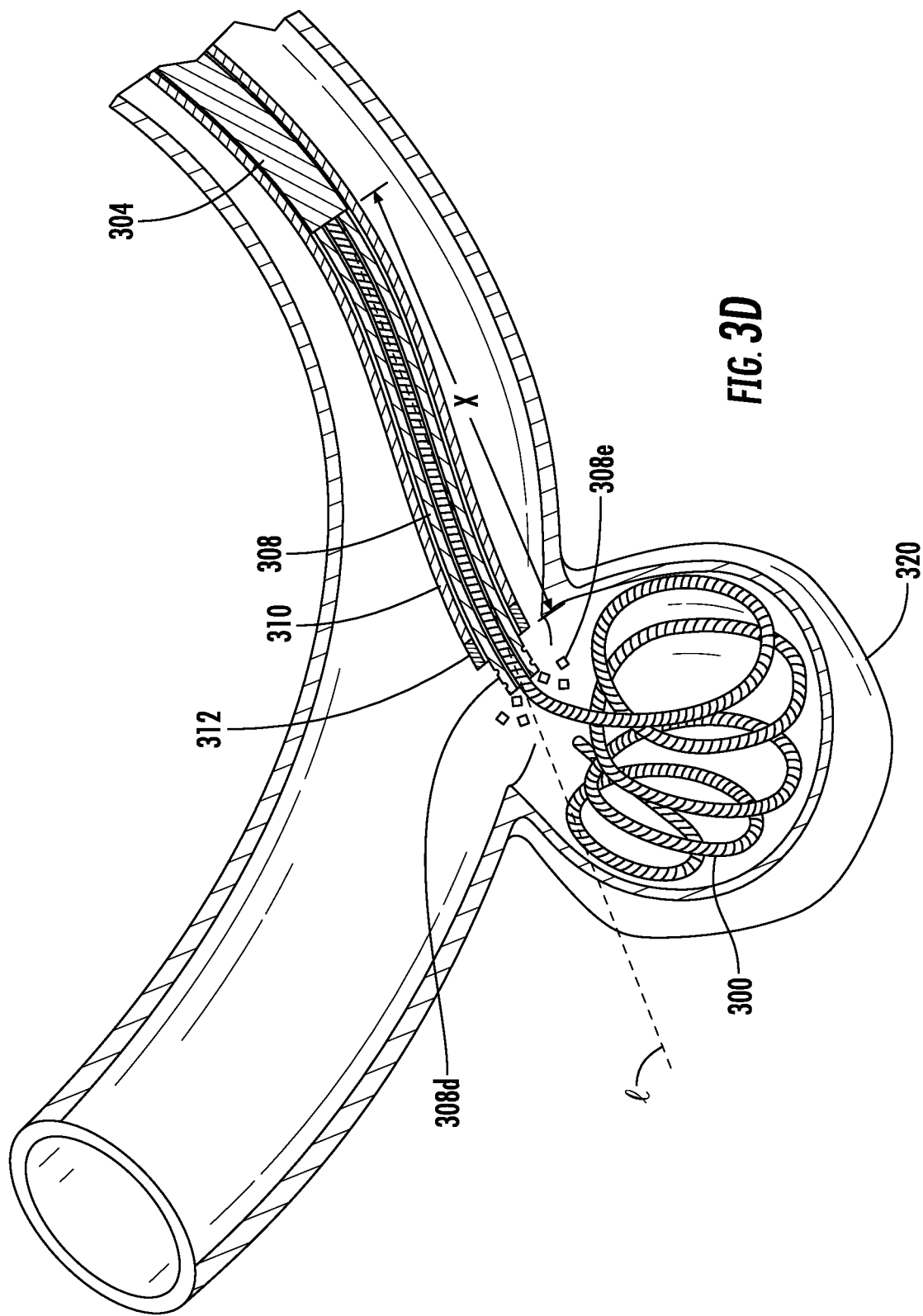
FIG. 3D schematically illustrates the coil of the embolic system of FIG. 3A being delivered at a second point in time, according to an embodiment of the present disclosure.

FIG. 3D illustrates the coil 300 of the embolic system of FIGS. 3A-3C being further delivered and deployed into the aneurysm 320. The delivery filament 304 is distally translated through the microcatheter 310 with a distal end of the delivery filament 304 abutting a proximal end of the coil 300. As the coil 300 continues to be distally translated out of the microcatheter 310 and substantially out of alignment with the longitudinal axis ℓ, the portion 308d of the coating 308 external to the microcatheter 310 continues to fracture and break away into particles 308e such that the coil 300 may further flex free of the coating 308 during deployment into the aneurysm 320. As the delivery filament 304 approaches a distance X away from the distal end of the marking band 312, the medical professional operating the system may visualize that the coil 300 is close to being fully deployed out of the microcatheter 310 (e.g., by employing a radiopaque delivery filament 304 that can be visualized by fluoroscopy) or may infer that the coil 300 is close to being fully deployed out of the microcatheter 310 based on the length of the delivery filament 304 that has been distally translated through the microcatheter 310. The distance X may be a variety of lengths, e.g., about 1 centimeter or the like. With the coil 300 almost fully deployed, the medical professional may reposition the coil 300 if necessary by manipulating the microcatheter 310 and/or translating the delivery filament 304. In various embodiments described herein, the delivery filament 304 and the coil 300 may be temporarily coupled to each other during delivery such that distal and proximal translation of the delivery filament 304 also translates the coil 300 in a similar manner, allowing for complete proximal removal and discard of the delivery filament 304 and the coil 300 if repositioning is difficult. For example, the delivery filament 304 may have geometry that substantially interlocks with complimentary geometry of the coil, e.g., a channel, a c-shaped link, or the like.

FIG. 3E illustrates the coil 300 of the embolic system of FIGS. 3A-3D being fully deployed into the aneurysm 320. Once a substantial portion of the coil 300 is confirmed to be in a desirably deployed position in FIG. 3D, the delivery filament 304 may be distally translated past the marking band 312 at the distal end of the microcatheter 310 for full deployment of the coil 300 (i.e., ejection of the coil 300 from the microcatheter 310. The remaining portion 308d of the coating is fracturing away from the coil 300 into the particles 308e such that the entire coil 300 may flex free of the coating for deployment into the aneurysm 320. If the delivery filament 304 is coupled to the coil 300, the delivery filament 304 may be manipulated, e.g., rotated, agitated, or the like, such that the coil 300 decouples from the delivery filament 304 external of the microcatheter 310. After deployment of the coil 300, an additional coil may be delivered and deployed through the microcatheter 310 in a similar manner if desirable, e.g., to further fill the aneurysm 320.

Figure 4:
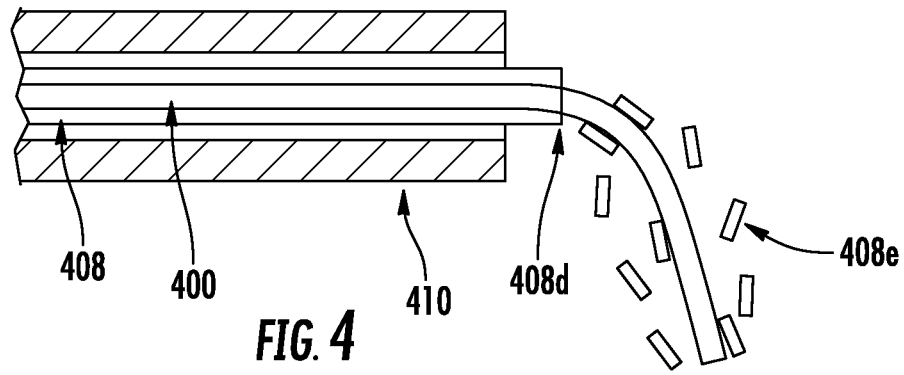
FIG. 4 schematically illustrates an embolic coil with a hydrophobic coating being deployed, according to an embodiment of the present disclosure.
Figure 5:
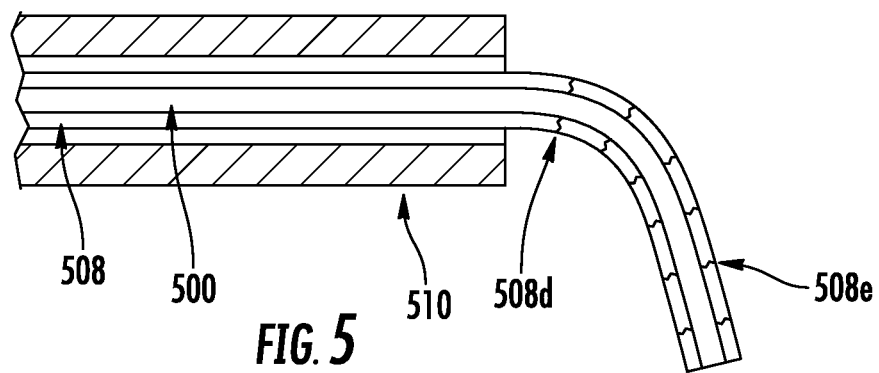
FIG. 5 schematically illustrates an embolic coil with a hydrophobic coating being deployed, according to an embodiment of the present disclosure.

With reference to FIGS. 4 and 5, in various embodiments described herein a coating 408, 508 of a coil 400, 500 may transition in various ways as the coil 400, 500 is deployed. For example, referring to FIG. 4, a coating 408 comprising a hydrophobic material may be substantially rigid during delivery within a microcatheter 410 (and/or a sheath or other elongate member, not illustrated), allowing the coil 400 to be distally advanced without prolapsing. As the coating 408 (i.e., a brittle coating) is distally extended out of the microcatheter 410 a portion 408d of the coating 408 is substantially misaligned with the microcatheter 410 and/or the proximal remainder of the coating 408 fractures away from the coil 400 into particles 408e, allowing the coil 400 to flex free of the coating 408 (e.g., for deployment). The particles 408e fracture away from the coil 400 because the coating 408 is not substantially adhered to the coil 400. Alternatively, referring to FIG. 5, a coating 508 may be substantially adhered to a coil 500 such that as a portion 508d of the coating 508 is distally extended out of a microcatheter 510 and misaligned with the microcatheter 510 and/or the proximal remainder of the coating 508, the portion 508d cracks along the coil 500 into an at least partially disjointed portion 508e (i.e., a brittle coating portion 508d cracking such that it is less rigid than prior to cracking), allowing the coil 500 to flex with the cracked coating 508e. The portion 508d of the coating cracks but is substantially maintained along the coil 500 because the coating 508 is substantially adhered to the coil 500. Such hydrophobic coatings 408, 508 may be more rigid (e.g., glass-like) in a substantially dry state and may not be rapidly plasticized by fluid. Such hydrophobic coatings 408, 508 may crack during coil 400, 500 deployment and, if there is substantial adhesion between the coating 408, 508 and the coil 400, 500, the coating 408, 508 may substantially remain along the deployed coil 400, 500. If the coating 408, 508 is not substantially adhered to the coil 400, 500, the coating 408, 508 may substantially fracture away from the deployed coil 400, 500 during or after deployment, biodegrade, and pass or metabolize within the body.

Figure 6:
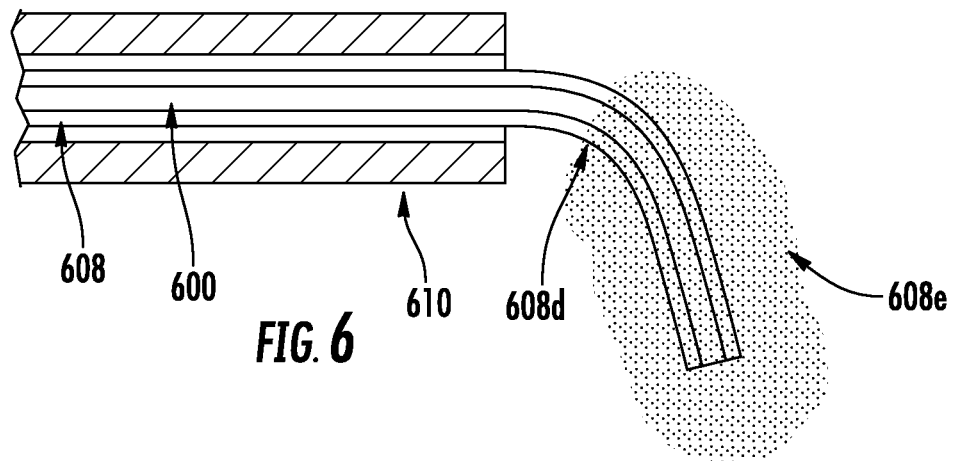
FIG. 6 schematically illustrates an embolic coil with a hydrophilic coating being deployed, according to an embodiment of the present disclosure.

With reference to FIG. 6, in various embodiments described herein a coating 608 of a coil 600 may become dissolved as the coil 600 is deployed. The coating 608 along the coil 600 comprises a hydrophilic material that may be substantially rigid during delivery within a microcatheter 610 (and/or a sheath or other elongate member, not illustrated), allowing the coil 600 to be distally advanced through the microcatheter 610 without prolapsing. As the coating 608 is distally extended out of the microcatheter 610 a portion 608d of the coating 608 is substantially exposed to and/or saturated in aqueous fluid (e.g., blood). The portion 608d of the coating 608 disperses into particles 608e and/or a solution away from the coil 600, allowing the coil 600 to flex free of the coating 608 for deployment. Such hydrophilic coatings 608 may be more rigid (e.g., glass-like) in a substantially dry state and may be rapidly plasticized by fluid, reducing rigidity. A duration of time for the coating 608 to plasticize in a fluid to a desirable flexibility may depend on the composition of the coating 608. In some embodiments, the coating 608 may flake off of the coil during and/or after coil 600 deployment.

All of the devices and/or methods disclosed and claimed herein can be made and executed without undue experimentation in light of the present disclosure. While the devices and methods of this disclosure have been described in terms of preferred embodiments, it may be apparent to those of skill in the art that variations can be applied to the devices and/or methods and in the steps or in the sequence of steps of the method described herein without departing from the concept, spirit and scope of the disclosure. All such similar substitutes and modifications apparent to those skilled in the art are deemed to be within the spirit, scope and concept of the disclosure as defined by the appended claims.

What is claimed is:

1. An embolic system, comprising:
   a microcatheter comprising a proximal end, a distal end, a longitudinal axis, and a working lumen therethrough;
   a sheath comprising a proximal end, a distal end, and a delivery lumen therethrough, the distal end of the sheath configured to be insertable within the working lumen at the proximal end of the microcatheter;
   a coil comprising a proximal end, a distal end, and a length therebetween slidingly disposed within the sheath;
   a coating disposed about the coil; and
   a delivery filament configured to be slidingly disposed within the sheath proximal of the coil such that the coil can be ejected from the distal end of the sheath into the working lumen of the microcatheter and configured to be slidingly disposed within the working lumen of the microcatheter proximal of the coil such that the coil can be ejected from the working lumen at the distal end of the microcatheter to a target site;
   wherein the coating is configured to substantially fracture as the coil transitions from being substantially aligned with the longitudinal axis of the microcatheter to substantially misaligned with the longitudinal axis of the microcatheter upon being ejected from the microcatheter or,
   wherein the coil comprises a primary shape that is substantially linear when disposed within the microcatheter and a secondary shape that is substantially curvilinear when ejected from the microcatheter to the target site, and
   wherein the coating is configured to substantially fracture away from the coil as the coil transitions from the primary shape to the secondary shape.

2. The embolic system of claim 1, wherein the coating is formed from a hydrophilic polymer having a number average molecular weight of about 10,000 g/mol to about 1,000,000 g/mol.

3. The embolic system of claim 1, wherein the coating is disposed about an outer surface of the coil.

4. The embolic system of claim 1, wherein the coil comprises a polymer and the coating comprises a hydrophilic polymer and wherein the coating is configured to substantially fracture upon being ejected from the microcatheter.

5. The embolic system of claim 1, wherein the coil further comprises a pro-thrombogenic factor covered by the coating.

6. The embolic system of claim 1, wherein the delivery filament comprises a distal end reversibly coupled to the proximal end of the coil.

7. The embolic system of claim 1, further comprising at least one fiber coupled to the coil and disposed within the coating.

8. An embolic coil, comprising:
   a coil filament arranged in adjacent windings about a longitudinal axis; and
   a coating disposed about the windings, wherein the coating is a frangible coating configured to fracture as a portion of the coil transitions from being substantially aligned with the longitudinal axis of a remainder of the coil;
   wherein the coil filament comprises a primary shape that is substantially linear and a secondary shape that is substantially curvilinear, and
   wherein the coating is configured to substantially fracture away from the coil filament as the coil filament transitions from the primary shape to the secondary shape.

9. The embolic coil of claim 8, wherein the coating comprises a hydrophilic polymer and wherein the coating is configured to fracture as the portion of the coil transitions from being substantially aligned with the longitudinal axis of the remainder of the coil.

10. The embolic coil of claim 8, wherein the coating is substantially insoluble while disposed about the windings and the coating is substantially soluble while fractured away from the windings.

11. The embolic coil of claim 8, wherein the coating comprises a hydrophilic polymer having a number average molecular weight of about 10,000 g/mol to about 1,000,000 g/mol.

12. An embolic coil, comprising:
   a coil filament arranged in adjacent windings about a longitudinal axis; and
   a coating disposed about the windings, wherein the coating is a frangible coating configured to fracture as a portion of the coil transitions from being substantially aligned with the longitudinal axis of a remainder of the coil;

wherein the coating is substantially insoluble while disposed about the windings and the coating is substantially soluble while fractured away from the windings.

13. The embolic coil of claim 12, wherein the coating comprises a hydrophilic polymer and wherein the coating is configured to fracture as the portion of the coil transitions from being substantially aligned with the longitudinal axis of the remainder of the coil.

14. The embolic coil of claim 12, wherein the coating comprises a hydrophilic polymer having a number average molecular weight of about 10,000 g/mol to about 1,000,000 g/mol.

* * * * *